US009404914B2

(12) United States Patent
Dahan et al.

(10) Patent No.: US 9,404,914 B2
(45) Date of Patent: Aug. 2, 2016

(54) MICROFLUIDIC SYSTEM FOR CONTROLLING A CONCENTRATION PROFILE OF MOLECULES CAPABLE OF STIMULATING A TARGET

(75) Inventors: Maxime Dahan, Paris (FR); Mathieu Morel, Paris (FR); Jean-Christophe Galas, Paris (FR); Vincent Studer, Bordeaux (FR); Denis Bartolo, Paris (FR)

(73) Assignees: Centre National de la Recherche Scientifique-CNRS, Paris (FR); Ecole Normale Supérieure, Paris (FR); Université Pierre et Marie Curie (Paris 6), Paris (FR); Fonds De L'ESPCI-Georges Charpak, Paris (FR); Univerité Bordeaux Segalen, Bordeaux (FR)

( * ) Notice: Subject to any disclaimer, the term of this patent is extended or adjusted under 35 U.S.C. 154(b) by 0 days.

(21) Appl. No.: 14/003,206

(22) PCT Filed: Mar. 2, 2012

(86) PCT No.: PCT/IB2012/051001
§ 371 (c)(1),
(2), (4) Date: Dec. 4, 2013

(87) PCT Pub. No.: WO2012/120424
PCT Pub. Date: Sep. 13, 2012

(65) Prior Publication Data
US 2014/0080206 A1 Mar. 20, 2014

(30) Foreign Application Priority Data
Mar. 4, 2011 (FR) ...................................... 11 00660

(51) Int. Cl.
G01N 33/50 (2006.01)
G01N 21/63 (2006.01)
(Continued)

(52) U.S. Cl.
CPC .......... *G01N 33/5008* (2013.01); *B01L 3/5027* (2013.01); *B01L 3/502753* (2013.01);
(Continued)

(58) Field of Classification Search
None
See application file for complete search history.

(56) References Cited

U.S. PATENT DOCUMENTS 5,885,470 A * 3/1999 Parce et al. .................... 216/33
7,374,906 B2 5/2008 Kirk et al.
(Continued)

FOREIGN PATENT DOCUMENTS

WO 2007/106451 A2 9/2007
WO 2008/009803 A2 1/2008
(Continued)

OTHER PUBLICATIONS

International Search Report issued in PCT/IB2012/051001 mailed on May 16, 2012 (6 pages).
(Continued)

*Primary Examiner* — Jennifer Wecker
(74) *Attorney, Agent, or Firm* — Osha • Liang LLP (57) ABSTRACT

The invention relates to a microfluidic system for controlling a concentration profile of molecules capable of stimulating a target, for example formed by an assembly of living cells, this system comprising: —a microfluidic device (1) comprising at least one microfluidic channel (4) equipped with at least one inlet orifice (21) and with at least one outlet orifice (22) for at least one fluid; —at least one means for supplying the microfluidic channel (4) with at least one fluid comprising molecules capable of stimulating the target; —at least one chamber (8) or another microfluidic channel comprising a base (6) intended to receive the target; and —at least one microporous membrane (5) separating the chamber (8) or the other microfluidic channel from the microfluidic channel (4), said microporous membrane (5) being positioned away from the base (6) so that when the supply means provides the microfludic channel (4) with said at least one fluid flowing in laminar flow in contact with the microporous membrane (5), the molecules capable of stimulating the target then diffuse, after having passed through the microporous membrane (5) through the chamber (8) or said other microfluidic channel in order to finally form a stable concentration profile in this chamber (8) or this other microfluidic channel.

20 Claims, 6 Drawing Sheets (51) Int. Cl.
  *B81B 1/00* (2006.01)
  *B01L 3/00* (2006.01)
  *C12M 3/06* (2006.01)

(52) U.S. Cl.
  CPC ....... *C12M23/16* (2013.01); *B01J 2219/00639* (2013.01); *B01L 3/502715* (2013.01); *B01L 3/502761* (2013.01); *B01L 2200/027* (2013.01); *B01L 2200/0647* (2013.01); *B01L 2200/0652* (2013.01); *B01L 2300/0627* (2013.01); *B01L 2300/0681* (2013.01); *B01L 2300/087* (2013.01); *B01L 2300/0816* (2013.01); *B01L 2300/0848* (2013.01); *B01L 2300/0851* (2013.01); *B01L 2300/163* (2013.01)

(56) References Cited

U.S. PATENT DOCUMENTS

| | | | | |
|---|---|---|---|---|
| 2002/0034818 | A1* | 3/2002 | Schillig | C12M 23/04 435/287.1 |
| 2004/0051154 | A1* | 3/2004 | Yamakawa et al. | 257/414 |
| 2004/0161369 | A1* | 8/2004 | Chan et al. | 422/82.05 |
| 2004/0245102 | A1* | 12/2004 | Gilbert | B01D 63/087 204/451 |
| 2005/0148064 | A1 | 7/2005 | Yamakawa et al. | |
| 2006/0108012 | A1* | 5/2006 | Barrow et al. | 137/806 |
| 2006/0185981 | A1* | 8/2006 | Turner | B01D 57/02 204/518 |
| 2006/0199260 | A1* | 9/2006 | Zhang et al. | 435/293.1 |
| 2007/0131611 | A1* | 6/2007 | Peng et al. | 210/500.27 |
| 2007/0272000 | A1* | 11/2007 | Kahl | B01L 3/502753 73/53.01 |
| 2008/0272000 | A1* | 11/2008 | Jacobson et al. | 204/450 |
| 2010/0025567 | A1* | 2/2010 | Lueerssen | 250/205 |
| 2010/0041128 | A1* | 2/2010 | Banes et al. | 435/287.9 |
| 2010/0197008 | A1* | 8/2010 | Handique et al. | 435/325 |
| 2010/0279396 | A1* | 11/2010 | Choi et al. | 435/294.1 |
| 2011/0020179 | A1* | 1/2011 | Yue et al. | 422/63 |
| 2011/0151479 | A1* | 6/2011 | Stevens et al. | 435/7.1 |
| 2013/0068310 | A1* | 3/2013 | Sip et al. | 137/1 |
| 2013/0130232 | A1* | 5/2013 | Weibel et al. | 435/5 |

FOREIGN PATENT DOCUMENTS

| | | |
|---|---|---|
| WO | 2008/028241 A1 | 3/2008 |
| WO | 2009/072715 A1 | 6/2009 |
| WO | 2010/013016 A2 | 2/2010 |

OTHER PUBLICATIONS

Kim, T. et al.; "Generating steep, shear-free gradients of small molecules for cell culture"; Biomed Microdevices (2009), vol. 11, pp. 65-73 (9 pages).
Written Opinion of the International Searching Authority issued in PCT/IB2012/051001 mailed on May 16, 2012 (4 pages).
French Search Report issued in FR1100660 dated Sep. 15, 2011 (2 pages).

* cited by examiner

this document.

MICROFLUIDIC SYSTEM FOR CONTROLLING A CONCENTRATION PROFILE OF MOLECULES CAPABLE OF STIMULATING A TARGET

The present invention relates to the field of microfluidics.

Microfluidics employs systems with micrometric dimensions, whose size is generally between a few tens and a few hundreds of microns.

These systems may be used in numerous fields such as cellular diagnostic tests, development of medicinal products, fundamental biology or cosmetology.

In these fields, there is an increasing demand for microfluidic systems for quantitative determination of the response of living cells to certain molecules and, in particular, the response to a concentration profile that is spatially and temporally controlled.

For example, it may be a question of measuring the response of cancer cells to molecules used for chemotherapy. Accurate determination of this response requires exerting a control of the use of the molecules that will produce this response. This control may relate to the quantity of molecules interacting with the cancer cells, the concentration profile of the molecules to which the cancer cells are exposed, the variation over time of the quantity of these molecules and/or of the concentration profile of these molecules used on the cancer cells, etc.

In the field of cosmetology, microfluidic systems can be used for testing the toxicity of certain molecules on living cells and/or cellular tissues. The control of the quantity of molecules, which may be toxic, administered to the cells and the manner in which these molecules are administered is necessary for determining the toxicity threshold.

An example of a microfluidic system widely used for stimulating living cells is presented in document U.S. Pat. No. 7,374,906. This microfluidic system notably allows the living cells to be submitted to a concentration gradient of molecules, whose profile is linear and stable over time.

A major drawback of this type of microfluidic system is that the living cells are submitted to a flow that generates shearing forces, perturbing them. This shearing effect is particularly troublesome when we aim to study the chemotactic response of the growth cone of nerve cells. Indeed, the flow generates shearing stresses that modify the response of the target cells in the best of cases, or that cause death or detachment of the cells.

The physiological behavior of the living cells studied in this way is perturbed with the system disclosed in this document.

Solutions have therefore been proposed for submitting living cells to a concentration gradient of molecules, without them being perturbed by a flow.

A microfluidic system for applying a concentration gradient of molecules likely to stimulate living cells is presented for example in the article "*Generating steep, shear-free gradients of small molecules for cell culture*", Taesung Kim, Mikhail Pinelis and Michel M. Maharbiz, Biomed Microdevices (2009), Vol. 11, pp. 65-73.

This microfluidic system comprises a microfluidic device 10 and means (not shown) for supplying the device with fluids.

Figure 1:
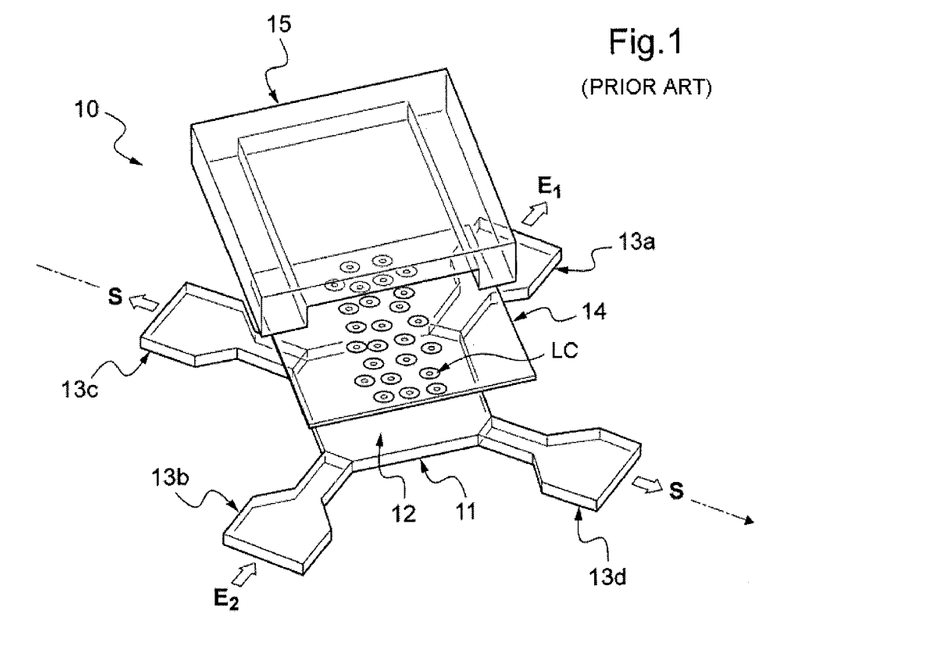
FIG. 1 is an exploded perspective view of a prior art microfluidic system.

The microfluidic system 10 disclosed in this document is shown in FIG. 1, in an exploded perspective view.

It comprises a polydimethylsiloxane (PDMS) base 11 comprising a central zone 12, of approximately square shape, connected to channels 13a, 13b, 13c and 13d arranged in the form of a cross relative to the central zone 12. It also comprises a polyester microporous membrane 14, covering the central zone 12 of the PDMS base 11. Finally, it comprises a PDMS cover 15, covering the polyester membrane 14, the PDMS base 11 and the channels 13a, 13b, 13c, 13d (the cover 15 is shown in truncated form in FIG. 1).

The microfluidic system 10 is thus separated in two parts by the polyester membrane 14.

A first part forms a channel in which moving fluids can circulate, said channel being closed at the top by the membrane 14, the lower side of the membrane thus forming a wall of this channel submitted to a flow.

A second part is formed by the upper side of the membrane 14, opposite the channel, and on which the living cells (LC) being cultured are located.

The means supplying the fluids are not shown. It should be noted, however, that a first fluid is introduced in the base 11 of the microfluidic system 10 via the inlet E1 and that a second fluid is introduced in this base 11 of the microfluidic system 10 via the inlet E2, opposite the inlet E1. At least one of these fluids comprises molecules intended to stimulate the living cells, by going through the polyester membrane 14.

The fluids entering via the inlets E1, E2 thus circulate in the base 11 of the microfluidic system 10, are brought in contact face to face, which creates a mixing zone at the interface of these two fluids, and then leave this base 11 via the outlets S.

For controlling the culture of the living cells over time as well as in space, it is possible, with the microfluidic system 10, to adjust the flow rates of the fluids in order to establish a predetermined concentration profile of molecules on the polyester membrane 14.

More precisely, after selecting the appropriate fluids, adjusting the flow rate of each of the two fluids allows to create a quite particular mixing zone at the interface between the two fluids, i.e. to create a quite particular concentration profile of molecules intended to stimulate the living cells. This mixing zone in which a concentration gradient is generated according to a defined profile extends roughly along an axis A, shown in FIG. 1, passing through the two outlets S of the base 11.

However, this microfluidic system has several drawbacks.

Firstly, the respective flow rates of the fluids from the inlets E1, E2 must be controlled very precisely in order to produce a concentration profile of molecules that is stable on the lower side of the polyester membrane 14.

This control of the fluid flow rates is performed upstream of the microfluidic system 10, namely at the fluid supplying means themselves, the gradient being generated for its part in the base 11, at the interface between the two fluids.

Thus, a perturbation of the flow rate of one or the other of the two fluids modifies the interface between the two fluids, and therefore the concentration profile of molecules on the lower side of the membrane 14 is also modified. The stability of the concentration profile is therefore difficult to achieve.

Moreover, since the living cells are arranged on the upper side of the membrane 14, the concentration profile applied on the living cells corresponds approximately to the profile applied on the lower side of the membrane. This is all the more true as the membrane 14 has a small thickness of 10 μm.

Secondly, the slope of the concentration profile obtained at the living cells depends on the fluid velocity in the microfluidic channel and of the position of the interface between the two fluids from the inlets E1, E2. The slope of the profile is therefore very difficult to control.

Thirdly, the microfluidic system 10 employs a polyester membrane 14, with its lower side stuck to the edges of the PDMS base 11, of square shape, and with its upper side stuck to the cover 15 made of PDMS. These materials are selected because they notably allow the membrane 14, the base 11 and the cover 15 to be stuck together by a process stated in this document. The presence of the cover 15 on the membrane 14 and the channels 13a, 13b, 13c, 13d allows to reinforce the mechanical resistance and hermeticity between the membrane 14 and the base 11, sticking between the membrane 14 and the base 11 being indeed only carried out on the edges of the base 11. Moreover, sticking of the membrane 14 is carried out with a deposit of prepolymer of PDMS, which allows irreversible manufacture of the device by heating under mechanical pressure. Once the membrane 14 and the cover 15 have been stuck, the cells can be inserted on the membrane 14, via openings left on the side of the cover 15.

With this arrangement and the selection of these materials, suitable mechanical resistance and hermeticity can thus be obtained.

To ensure hermeticity between the channel and the membrane 14, the microfluidic system must be closed by the cover. It is then necessary to carry out the culture of the cells inside the microfluidic system 10. This is not very practical for complex cell cultures, such as primary cultures of neurons, explants or slices of tissues.

Moreover, with a PDMS cover 15, the response of the living cells to stimulation cannot be visualized, or is difficult to visualize. This is all the more critical as a PDMS cover must have a certain thickness to allow its manipulation, as this material has a low elastic modulus. A large thickness decreases the optical qualities of this material even further. It is therefore very difficult to observe, by a suitable optical means, the response of the living cells arranged on the membrane.

One objective of the invention is to overcome at least one of these drawbacks.

To achieve at least one of these objectives, the invention proposes a microfluidic system for controlling a concentration profile of molecules likely to stimulate a target, for example formed by a set of living cells, the system comprising:
 a microfluidic device comprising at least one microfluidic channel provided with at least one inlet orifice and at least one outlet orifice for at least one fluid;
 at least one means for supplying the microfluidic channel with at least one fluid comprising molecules likely to stimulate the target;
 at least one chamber or another microfluidic channel having a base intended to receive the target; and
 at least one microporous membrane separating the chamber or the other microfluidic channel from the microfluidic channel,
said microporous membrane being arranged away from the base so that when the supplying means supplies, to the microfluidic channel, said at least one fluid flowing under a laminar regime in contact with the microporous membrane, the molecules likely to stimulate the target then diffuse, after going through the microporous membrane, through the chamber or said other microfluidic channel and finally form a stable concentration profile in this chamber or this other microfluidic channel.

The system can envisage other technical features, either alone or in combination:
 the microfluidic channel comprises a cover made of a material selected from: glass or silicon, a non-elastomeric photocrosslinked polymer, a metal, an alloy that is an electrical conductor or semiconductor, a ceramic, quartz, sapphire, an elastomer;
 said at least one inlet orifice and said at least one outlet orifice for the fluids are formed in the cover;
 the microfluidic channel comprises at least one wall made of a photo-cured and/or thermally cured resin;
 the microporous membrane extends transversely on the side wall of the microfluidic channel to close said channel at the bottom;
 the microfluidic channel is organized on several levels, each level having at least one inlet orifice for at least one fluid;
 the base of the chamber or of said other microfluidic channel is made of an optically transparent material;
 the chamber or said other microfluidic channel comprises side walls made of a photo-cured and/or thermally cured resin;
 the microporous membrane extends transversely between the side walls of the chamber or of said other microfluidic channel to close said chamber or said other microfluidic channel at the top;
 the microporous membrane is made of a material selected from: glass, polycarbonate, polyester, polyethylene terephthalate, quartz, silicon, silica or silicon carbide;
 the microporous membrane comprises pores with a density between $10^3$ and $10^{10}$ pores/cm$^2$;
 the pores have a hydraulic diameter between 0.05 µm and 12 µm, preferably between 0.05 µm and 3 µm;
 it comprises a optical visualization means;
 the optical means employs a technique of photoactivated localization microscopy or a technique of stimulated emission depletion microscopy.

Other features, aims and advantages of the invention will be presented in the following detailed description, referring to the following figures.

The invention relates to a microfluidic system for controlling a concentration profile of molecules likely to stimulate a target, for example formed by a set of living cells, the system comprising a microfluidic device and at least one means for supplying this device with at least one fluid comprising molecules likely to stimulate this target.

The microfluidic device is described with reference to FIG. 2 and a process of manufacture of this device is described with reference to FIGS. 3(a) to 3(d) and 4(a) to 4(c). We shall then describe, as non-limiting examples, particular forms of microfluidic channel that can be used within this device, with reference to FIGS. 5(a) and 6(a).

Figure 2:
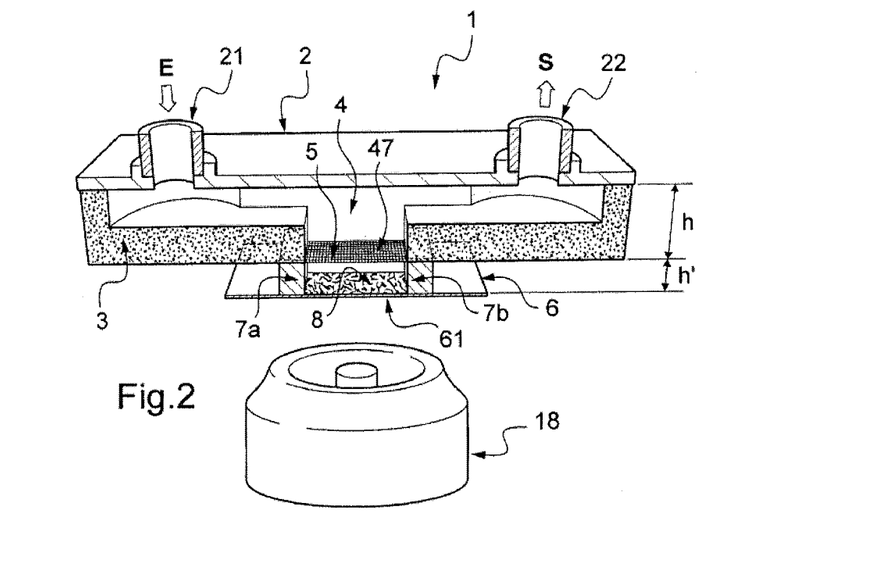
FIG. 2 is a diagram of a microfluidic device according to the invention, in a partially sectional, perspective view.

FIG. 2 shows a microfluidic device 1 according to the invention, in a partially sectional, perspective view.

This microfluidic device 1 comprises a cover 2, advantageously rigid, provided with two orifices 21, 22, and a side wall 3 advantageously made of a photo-cured and/or thermally cured resin. The side wall 3 of the device 1 is produced as a single layer of a photo-cured and/or thermally cured resin.

The microfluidic device 1 also comprises, in its lower part, an opening 47 covered by a microporous membrane 5 extending transversely to the base of the side wall 3. The side wall 3, the cover 2 and the microporous membrane 5 allow to define a microfluidic channel 4, the inlet and the outlet of which consist of said orifices 21, 22.

The microporous membrane 5 prevents the fluid, intended to flow in the microfluidic channel 4, from going to the other side of this membrane, the latter allowing, however, diffusion of the molecules likely to stimulate the target, which are carried by the fluid in the microfluidic channel 4.

The microfluidic device 1 also comprises a base 6, advantageously rigid and transparent, and side walls 7a, 7b, advantageously made of a photo-cured and/or thermally cured resin. These side walls 7a, 7b, the base 6 and the microporous membrane allow to form a chamber 8, constituting a culture chamber for the target cells. To form the chamber 8, four side walls are provided, but in reality these walls can be likened to a single outline, as the process of manufacture advantageously produces these walls in one piece.

The bottom of the chamber 8 is formed by the upper side 61 of the base 6, which is intended to receive the target, for example formed from living cells. Therefore, the living cells are not intended to be arranged on the microporous membrane 5, but away from the latter, on the base 6 of the chamber 8. They can thus be cultivated in standard conditions, separately from the microfluidic device 4.

The microporous membrane 5 thus separates the device into two separate microfluidic channels 4, 8. The microfluidic channel 4 allows to circulate a fluid comprising molecules likely to stimulate the target. This is carried out, as will be explained in more detail later in the description, by diffusion through the microporous membrane 5 to the chamber 8, and then by diffusion through the chamber 8 (culture chamber), at the bottom of which there are, for example, living cells (LC) that are to be stimulated.

Advantageously, the base 6 is made of an optically transparent material, for example glass. This is interesting because it is then possible to arrange an optical visualization means outside of the device, to visualize, for example, the response to a stimulation of the living cells arranged at the bottom of the chamber 8.

The cover 2 can be made of a material selected from: glass or silicon, a non-elastomeric photocrosslinked polymer, a metal, an alloy that is an electrical conductor or semiconductor, a ceramic, quartz, sapphire, an elastomer.

The size of the pores of the microporous membrane 5 is selected to prevent any passage of fluid between the first microfluidic channel 4 and the chamber 8. If the pores are cylindrical, this size is comparable to the pore diameter. More generally, the size of a pore can be likened to the hydraulic diameter of the latter.

In reality, the microporous membrane 5 cannot be completely impervious to a passage of fluid. Accordingly, it can be considered that the cells located at the bottom of the chamber 8 are not submitted to any flow if the flow-through velocity of the fluid through the microporous membrane 5 is below a limit value.

For example, it can be considered that this limit velocity is of the order of 1 µm/s. In this case, the shearing stresses imposed on the cells are negligible, even for a chamber 8 having a small height h', for example of 20 µm.

Moreover, the velocity in the microfluidic channel 4 will generally be between 100 µm/s and 1000 µm/s.

Thus, to obtain the limit value of 1 µm/s, the hydraulic resistance $R_{h,membrane}$ of the microporous membrane 5 must be, depending on the velocity of the fluid in the channel 4, from 100 to 1000 times greater than the hydraulic resistance $R_{h,channel}$ of the microfluidic channel 4.

In particular, if the flow velocity of the fluid in the microfluidic channel 4 is 1000 µm/s, it is necessary to observe the inequality:

$$1000 * R_{h,channel} < R_{h,membrane} \tag{R1}$$

to ensure that the velocity of the fluid through the membrane 5 is well below the considered limit value of 1 µm/s.

Moreover, if we consider a rectangular microfluidic channel 4 of height h, width w and length L, and a microporous membrane 5 of thickness e and having pores that are identical and cylindrical with a radius $r_{pore}$, with a surface pore density ρ, then the relation (R1) is written in the form:

$$1000 * \mu \cdot L/(w \cdot h) < \mu \cdot e/(r_{pore}^4 \cdot \rho \cdot Lw) \tag{R2}$$

and:

$$\theta = r_{pore}^4 \cdot \rho/e < 10^{-3} * h^3/L^2 \tag{R3}$$

For a microfluidic channel 4 of height h=100 µm, width w=1000 µm and length L=1000 µm, then the term θ must be less than $10^{-9}$ m to fulfill relation (R3). Moreover, if we consider cylindrical pores of radius 1 µm and a membrane thickness of 10 µm, then the surface pore density ρ must be less than $10^6$ pores/cm².

The relation (R3) can of course be generalized as a function of the considered value of the limit velocity of the fluid going through the microporous membrane 5 on the one hand, and of the flow velocity of this fluid in the microfluidic channel 4 on the other hand.

The microporous membrane 5 can have pores whose hydraulic diameter is between 0.05 µm and 12 µm. In particular, if the pore is cylindrical, then the hydraulic diameter of the pore corresponds to its diameter.

Advantageously, this hydraulic diameter will, however, be between 0.05 µm and 3 µm. Indeed, it should be noted that the use of a membrane with pores whose hydraulic diameter is below 3 µm will prevent all passage of flow in the chamber 8, for most conditions of use likely to be encountered.

At present, membrane manufacturers offer membranes whose hydraulic diameter of the pores is generally above 0.2 µm. In the context of the invention, the pores can therefore have hydraulic diameters advantageously between 0.2 µm and 3 µm. However, in theory, there is no lower limit for the hydraulic diameter of the pores, which explains why it is conceivable to employ pores whose hydraulic diameter reaches 0.05 µm.

If larger pores are used, the microfluidic device is however more difficult to use (for example in the choice of the flow rates in the microfluidic channel 4) to ensure that the fluid does not go through the microporous membrane 5.

As for the pore density, it can be between $10^3$ and $10^{10}$ pores/cm². The height of the pores can be between 50 nm and 100 µm.

Moreover, the microporous membrane 5 can be made of various materials such as glass, quartz, silicon, silica or silicon carbide, or polymers of the same nature as the polymers likely to be used for the rest of the microfluidic device. Thus, polycarbonate, polyester or polyethylene terephthalate can be used.

According to a first example, a polycarbonate microporous membrane 5 can be envisaged, in which the hydraulic diameter of the pores is between 0.2 µm and 1 µm, for example of the Cyclopore type from the company Whatman (Whatman Cyclopore™). According to a second example, a polyester microporous membrane 5 can be envisaged, in which the hydraulic diameter of the pores is between 0.4 µm and 3 µm, for example of the Transwell type from the company Corning (Corning® Transwell®). According to a third example, a polyethylene terephthalate microporous membrane 5 can be envisaged, in which the hydraulic diameter of the pores is between 0.4 µm and 8 µm, for example of the "Track-Etched" type from the company Becton Dickinson.

These microporous membranes have the advantage of being compatible with a process of manufacture of the microfluidic device 1 that is described below, with reference to FIGS. 3(a) to 3(d). They also have the advantage of being biocompatible and functionalizable to be specifically permeable to various molecules. "Functionalizable" means that the microporous membrane 5 can be chemically modified to fulfill a particular function (retention of certain species, chemical reactions, etc.).

In general, the device may have the following dimensions. The height h of the microfluidic channel can be between 1 µm and 1000 µm, advantageously between 10 µm and 200 µm. Its width (not shown) can be between 10 µm and 2 mm. The height h' of the chamber 8 can be between 10 µm and 1000 µm, advantageously between 50 µm and 200 µm. Moreover, the distance between the inlet E and the outlet S is of a few centimeters.

An example of a process of manufacture of the microfluidic device 1 according to the invention is a process that comprises at least the steps consisting of:
  (a) using a stamp 1' made of an elastomeric material to print a photo-curable and/or thermally curable liquid placed on a substrate 2' provided with the microporous membrane 5;
  (b) photo-irradiating and/or heating the liquid L to form a first side wall 3 closed at its base by the microporous membrane 5;
  (c) sticking the cover 2 provided with at least two orifices 21, 22 on the first side wall 3, on the side opposite the substrate 2' to form the microfluidic channel 4, in which a fluid can circulate;
  (d) after having removed the substrate 2', sticking on the part of the first side wall 3, made accessible by removing the substrate 2', an assembly comprising at least the base 6 and said at least two second side walls 7a, 7b made of a photo-cured and/or thermally cured resin, to form the chamber 8.

This process is based on the process disclosed in document WO 2008/009803.

Figure 3A:
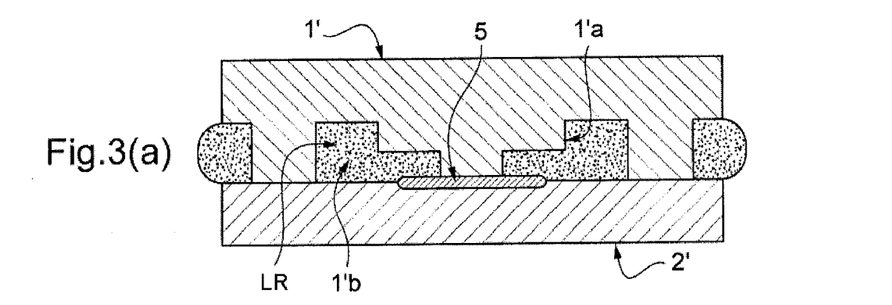
FIGS. 3(a) to 3(d) show, as appropriate, steps of a process of manufacture of the microfluidic device shown in FIG. 2 or intermediate structures obtained at the end of certain steps of this process.

The operation carried out during step (a) is shown in FIG. 3(a).

The stamp 1' used in step (a) can be made of an elastomeric material such as PDMS. It has a profile used as a mold that is complementary to that of the microfluidic device 1 that we wish to produce. The stamp 1' thus has a projection 1'a corresponding to the channel 4 of the microfluidic device 1 that we wish to obtain. It also has a hollow zone 1'b surrounding the projection 1'a, which is the zone in which said first side wall 3 of the microfluidic device 1 is intended to be formed. The substrate 2' can also be made of PDMS and has a flat profile.

The microporous membrane 5 is arranged beforehand on the substrate 2', then the stamp 1' is pressed against the substrate 2'. The stamp 1' thus wedges the membrane 5 against the substrate 2' via the projection 1'a.

Next, the photocrosslinkable and/or photopolymerizable resin in liquid form LR fills the volume located between the stamp 1' and the substrate 2' in an appropriate amount, notably in the hollow zone 1'b of the stamp 1'. This filling does not alter the position of the microporous membrane 5, as the latter is wedged between the stamp 1' and the substrate 2'.

The photocrosslinkable and/or photopolymerizable resin is a solution or a dispersion based on monomers and/or prepolymers. Photocrosslinkable and/or photopolymerizable resins usually employed as adhesives, glues or surface coatings are used in the process of the invention.

Advantageously, adhesives, glues or surface coatings usually employed in the field of optics are selected. Such resins, once they have been irradiated and photocrosslinked and/or photopolymerized, become solid. Preferably, the solid thus formed is transparent, and free of bubbles or any other irregularity.

Such resins are generally based on monomers/comonomers/prepolymers of the epoxy, epoxysilane, acrylate, methacrylate, acrylic acid, or methacrylic acid type, but we may also mention thiolene, polyurethane, and urethane-acrylate resins. The resins can be replaced with photocrosslinkable aqueous gels such as polyacrylamide gels and they are selected to be liquid at room temperature. The resins can also be replaced with polydimethylsiloxane (PDMS).

Among the photocrosslinkable resins usable in the present invention, we may mention the products marketed by the company Norland Optics under the trademark NOA® Norland Optical Adhesives, for example the products NOA81 and NOA60, the products marketed by the company Dymax in the range "Dymax Adhesive and light curing systems", the products marketed by the company Bohle in the "UV adhesives" range, the products marketed by the company Sartomer under the commercial references SR492 and SR499.

The polymerization and/or crosslinking of these resins is carried out by photoactivation using any suitable means, such as an irradiation with UV, visible, or IR radiation.

Preferably, a resin is selected which, once polymerized and/or crosslinked, is rigid and non-flexible, since the elastomeric resins tend to deform when fluids are circulated under pressure in the microfluidic device 1. However, for certain applications, such as the study of the elasticity of living cells, the use of photocrosslinkable elastomeric resins is not ruled out.

After filling the volume located between the stamp 1' and the substrate 2' with the liquid resin LR, a pressure P is applied on the stamp 1' to drive out any possible surpluses of resin. In FIG. 2, the projecting parts and notably the projection 1'a of the elastomeric stamp 1' are in contact with the substrate 2'. The liquid resin assumes the shape of the hollow zones of the stamp 1'.

Figure 3B:
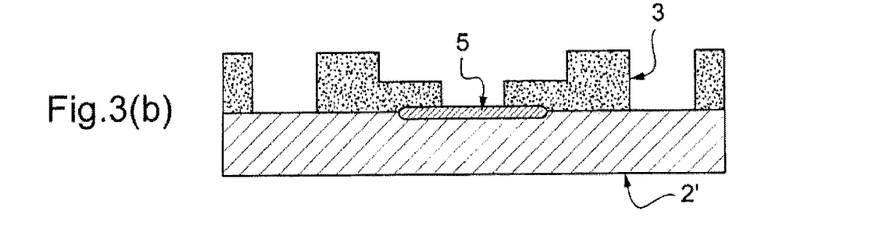

The structure obtained at the end of step (b) is shown in FIG. 3(b).

During step (b), the irradiation of the resin is carried out in the axis perpendicular to the base of the device, through the stamp 1'. The irradiation must be correctly proportioned so that, if required, active polymerization and/or crosslinking sites are left on the surface of said first resin side wall 3. Then, the stamp 1' is removed from the device. FIG. 3(b) shows the first side wall 3 made of a photopolymerized and/or photocrosslinked resin, with a profile complementary to that of the hollow zones of the stamp 1'.

It is understood that it is possible to envisage the profile of the stamp 1' to be such that the photopolymerized and/or photocrosslinked resin defines other patterns. This is notably the case for the microfluidic device 100 according to the invention, which will be further described with reference to FIG. 9.

The printing with an elastomeric stamp 1' in a resin in the liquid state allows to obtain structures of very small size with a very good resolution.

Figure 3C:
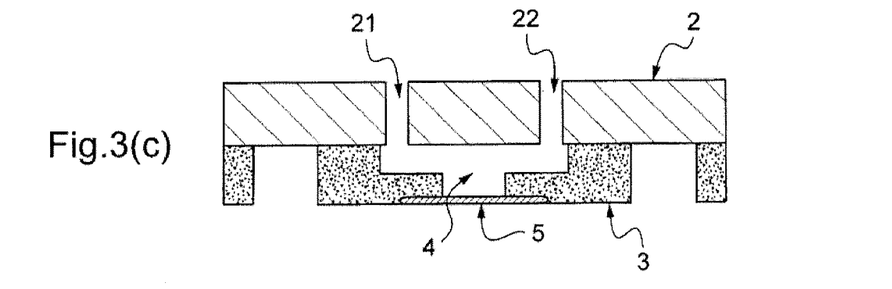

Then, during step (c), the cover 2 having at least two orifices 21, 22 is fixed on the device, on the side of said first side wall 3 previously in contact with the stamp 1'. The substrate 2' can then be removed.

The structure obtained at the end of step (c) is shown in FIG. 3(c).

The removal of the substrate 2' is carried out without the microporous membrane being unstuck from the photopolymerized and/or photocrosslinked resin, and without it being pulled out or partially torn.

The cover 2 can be made of glass, silicon, a solid polymer film, a metal, an alloy that is a conductor or semiconductor, a ceramic, quartz, sapphire, an elastomer.

A glass slide, a polymer film or a silicon slide is preferably selected. The materials used for forming the cover 2 are selected depending on the intended application of the microfluidic device 1.

Thus, a cover 2 made of an optically transparent material, such as glass, is more suitable for facilitating the observation, and the optical detection (transparency). Another advantage of glass is its very good thermal conductivity, which allows uniform heating of the devices.

It should be noted that the arrangement of the microporous membrane 5 at the lower part of the microfluidic channel 4 makes its use compatible with the standard protocols for culture of living cells. Indeed, it can then be envisaged that the base 6 is a glass slide on which living cells are cultured, said slide then being fixed on the structure obtained at the end of step (c) to form the chamber 8 (culture chamber), as is explained later in the description.

Figures 4A, 4B, 4C:
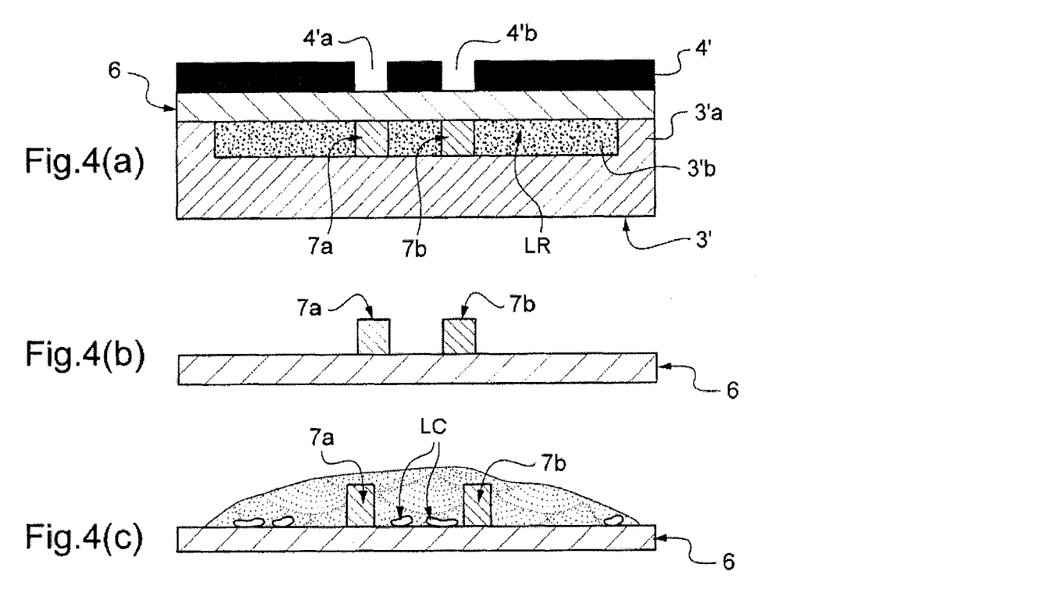
FIGS. 4(a) to 4(c) show intermediate structures obtained during the manufacture of an assembly formed by a base and side walls of the device, said assembly being intended to form a part of the microfluidic device of FIG. 2.

The assembly comprising a base 6 and two second side walls 7a, 7b can be produced on the basis of the following process steps:

($e_1$) using an open mold 3' made of an elastomeric material having a substrate side 3'a and a cavity 3'b intended to receive a photo-curable and/or thermally curable liquid resin LR;

($e_2$) arranging the base 6 on the substrate side 3'a of the mold 3';

($e_3$) arranging a mask 4' on the base 6, then photo-irradiating or heating to form said second side walls 7a, 7b.

The structure obtained at the end of steps ($e_1$) to ($e_3$) is shown in FIG. 4(a), in the case where step ($e_3$) consists of photo-irradiating the liquid resin.

The mold 3', like the stamp 1' and the substrate 2', can be made of an elastomer such as PDMS.

The photo-curable and/or thermally curable liquid resin used to form the walls 7a, 7b can be selected from the possibilities already described for the liquid resin used in step (a). Preferably, the liquid resins used for steps (a) and ($e_1$) to ($e_3$) are the same. As a variant, it would be possible to use photocrosslinkable aqueous gels such as those described above, or polydimethylsiloxane (PDMS).

The base 6 can be selected from the materials used for the cover. Advantageously, an optically transparent material can be used, to facilitate the optical visualization by a dedicated device. This optically transparent material can notably be glass, the base 6 thus forming a glass cover as is usually employed for the culture of living cells (LC). Moreover, using glass allows to take advantage of the chemical and biological surface treatments that are already available for this substrate.

The mask 4' can have orifices 4'a, 4'b allowing photo-irradiation of the precise zones of the liquid resin in order to form said second side walls 7a, 7b of the microfluidic device.

Once step ($e_3$) is completed, all that remains is to remove the mask 4' and the mold 3' in a step ($e_4$) to leave just the assembly formed by said second side walls 7a, 7b and the base 6. This assembly is shown in FIG. 4(b).

Generally, a step ($e_5$) is then performed, consisting of rinsing said assembly, for example with an ethanol/acetone mixture in proportions 90/10 by volume. This rinsing allows to remove all the resin that has not been photo-irradiated or has not been heated likely to remain on the base 6.

Then, living cells (LC) are cultured before arranging this assembly with the structure obtained at the end of step (c) and before beginning step (d).

For this, it is necessary to make the assembly biocompatible.

For this purpose, the assembly can be strongly photo-irradiated, for example with UV, followed by a vigorous rinsing in a neutral solution, such as water, for several hours.

Finally, a culture of living cells can then be carried out on the upper side 61 of the base 6, as shown in FIG. 4(c). This culture is carried out in standard conditions. In particular, said culture can be carried out on a base 6 that is in the form of a conventional glass slide.

Figure 3D:
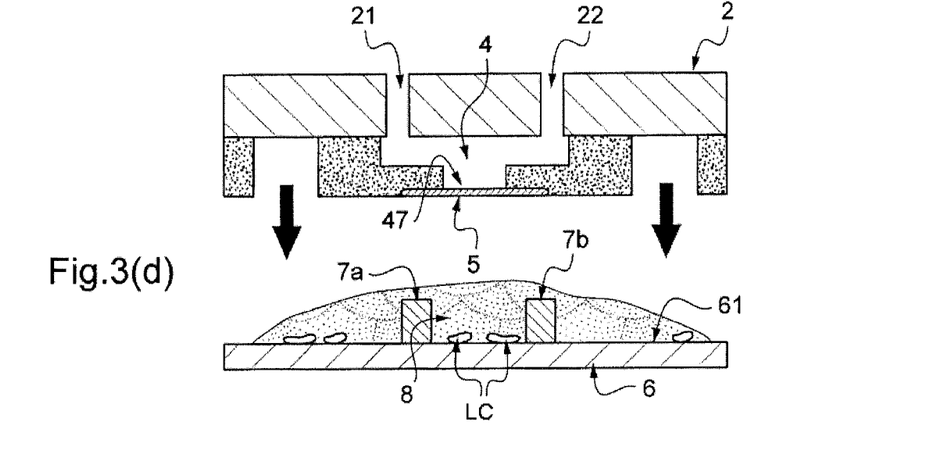

Once this culture is completed, step (d) can be carried out. The operation carried out in step (d) is shown in FIG. 3(d).

Once step (d) has been carried out, the microfluidic device 1 is ready to be used. It notably comprises living cells on the upper side 61 of the base 6, which is opposite the microporous membrane 5 within the chamber 8 (culture chamber).

To use this microfluidic device 1, it is combined with a fluid supplying means (not shown) which also belongs to the microfluidic system according to the invention. This supplying means allows to supply the microfluidic channel with at least one fluid comprising molecules likely to stimulate living cells.

This supplying means can for example be formed from a set of fluid tanks, connected to the microfluidic channel 4 by capillaries. With this means, it is then possible to perform dilutions and/or mixtures of the different fluids received from the different reservoirs, before they enter the microfluidic channel.

Moreover, the microfluidic channel 4 can have a particular shape.

Figure 5A:
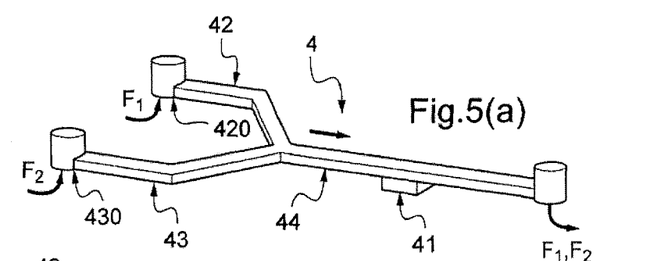
FIG. 5(a) shows a microfluidic channel of the microfluidic device according to the invention.

An example of microfluidic channel 4 likely to be used is shown schematically in FIG. 5(*a*), in a perspective view.

It is a microfluidic channel 4 for two different fluids $F_1$, $F_2$. The fluids $F_1$, $F_2$ only differ by the presence, in one of the two fluids and at low concentration, of stimulation molecules for the target cells. The fluids are conveyed in two branches 42, 43 which combine in a common branch 44 having an interface 41 on which the microporous membrane 5 of the microfluidic device 1 is intended to be arranged.

It is understood that, in this particular case, the supplying means provides two sources of fluid, for the fluids $F_1$, $F_2$ respectively.

These fluids $F_1$, $F_2$ are introduced in the microfluidic channel 4 via the inlets 420, 430. Moreover, the end of the common branch 44 has a common outlet 45 for the two fluids $F_1$, $F_2$. The general shape of the microfluidic channel 4 is a Y shape.

It should be noted that the inlets 420, 430 are to be compared with the inlet orifice 21 in FIG. 2 and that the outlet 45 is to be compared with the outlet orifice 22 in FIG. 2. In FIG. 2, the microfluidic channel 4 is designed for circulating just a single fluid, entering by a single orifice 21 and leaving by a single orifice 22.

Figure 5B:
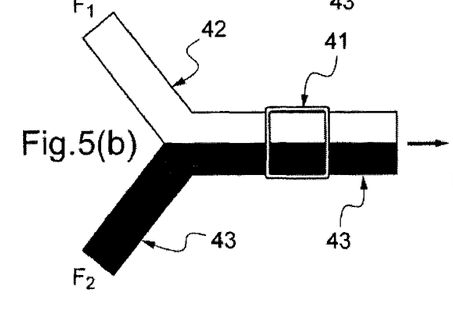
FIG. 5(b) shows fluids flowing in this first channel according to the invention and FIG. 5(c) shows a concentration profile obtained in a chamber of the device according to the invention.

FIG. 5(*b*) is a schematic representation of the flow of the fluids $F_1$, $F_2$ in the different branches of the microfluidic channel 4. In particular, it is noted that, in the common branch 44, the fluids $F_1$, $F_2$ flow in laminar regime, alongside one another. As the flow is laminar, the fluids do not mix hydrodynamically.

As is known, the flow is considered to be laminar if the Reynolds number of the flow in this common branch 504 is below a critical Reynolds number, which can be easily determined from fluid mechanics handbooks.

The Reynolds number is a dimensionless number defined by the relation $Re=(V\cdot D_h)/v$ where V is the velocity of the fluids in the common branch 44, $D_h$ is the hydraulic diameter of the common branch 44 and v is the kinematic viscosity of the fluids. The hydraulic diameter depends on the geometry of the common branch 44.

Taking into account the shape of the microfluidic channel, the critical Reynolds number is of the order of 2300.

Taking into account the nature of the flow, we speak of a supplying means of the "co-flow" type.

In practice, as the dimensions of the microfluidic channel 40 are micrometric, the flow is laminar for the fluids and the flow velocities of these fluids usually used for the applications envisaged by the invention.

These fluids $F_1$, $F_2$ are intended to flow in the microfluidic channel 4 of the microfluidic device 1, both in contact with the microporous membrane 5, but not in the chamber 8 (culture chamber).

Conveying the molecules (contained in at least one of the two fluids $F_1$ or $F_2$) likely to stimulate the living cells, between the microfluidic channel 4 and said cells disposed on the base 6 of the chamber 8, then takes place by diffusion in the chamber 8, through the microporous membrane 5.

More precisely, conveying these molecules takes place firstly by diffusion through the microporous membrane 5, then by diffusion through the chamber 8, finally reaching the upper side 61 of the base 6 of the chamber 8, namely side 61 on which the living cells are located.

However, it takes a certain time for the concentration profile to stabilize in the chamber. In particular, at the base 6 of the chamber 8, the stabilization time $t_{stab}$ is of the order of $h'^2/D$ where h' is the height of the chamber 8 and D is the diffusion coefficient of the molecules intended to stimulate the target cells in the chamber 8. It should be noted that to avoid excessive stabilization times, the height of the chamber will generally be limited to 500 μm.

Figures 6A, 6B, 6C:
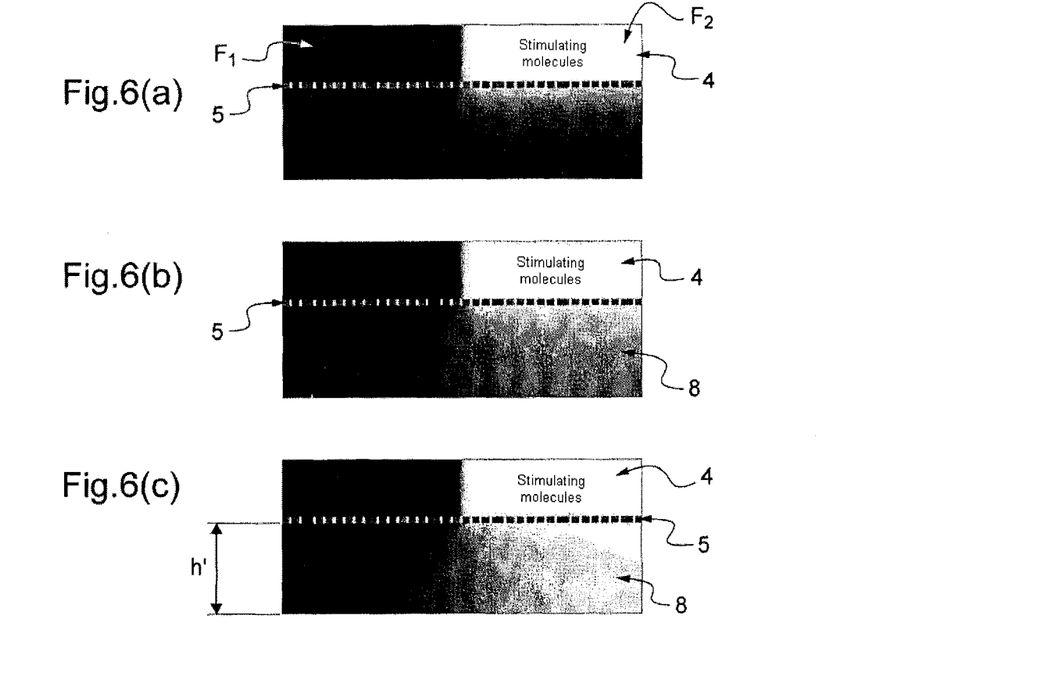
FIGS. 6(a) to 6(c) all show the microfluidic device according to the invention in a sectional view, for which can be observed successively different steps of the stabilization, over time, of a concentration profile of molecules intended to stimulate living cells in the chamber of the device.

FIGS. 6(*a*) to 6(*c*) show several steps in the diffusion phenomenon, when considering a fluid supply of the "co-flow" type. In white, the fluid $F_2$ comprises stimulation molecules for the living cells intended to be placed on the base 61 of the chamber 8. In black, the fluid $F_1$ is neutral. In FIG. 6(*a*), the fluid supply arrives at the microporous membrane 5 and the molecules begin to diffuse in the chamber 8. In FIG. 6(*b*), we are in a transitional regime where the concentration profile is in the stabilization phase. In FIG. 6(*c*), the concentration profile has stabilized.

It is understood that the diffusion takes place principally over the height of the chamber 8 (culture chamber), i.e. a direction that is approximately perpendicular to the flow direction of the fluids $F_1$, $F_2$ in the microfluidic channel 4, even if this diffusion in the chamber 8 also takes place in the other directions.

Figure 5C:
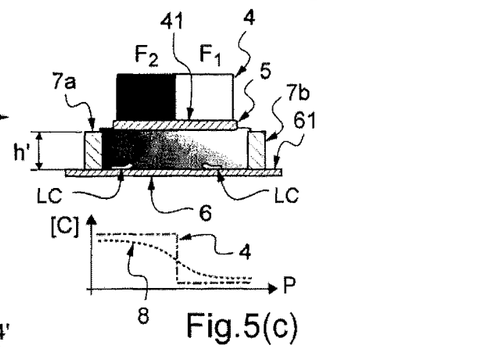

FIG. 5(*c*) shows, in a sectional view, what happens at the interface 41 with the microfluidic device 1.

For this, an experiment was performed with a neutral solution as first fluid $F_1$ and a fluorescent solution as second fluid $F_2$. The fluorescent solution $F_2$ comprises molecules having a diffusion coefficient similar to that of the molecules usually used for the stimulation of living cells. In this case, the fluorescent solution used can be fluorescein isothiocyanate, can comprise a fluorescent protein called GFPuv for "Green Fluorescent Protein" or can comprise a protein associated with dextran-70MW-rhodamine fluorescent molecules. This is the protein dextran-70 coupled to fluorescent molecules of rhodamine-B.

Above the microporous membrane 5, namely in the microfluidic channel 4 of the microfluidic device 1, the concentration profile of the fluorescent solution shown in FIG. 5(*c*) is in the crenelations (as in FIG. 6(*c*) moreover). Indeed, this fluorescent solution only occupies a part of the microfluidic channel 4, the other part of said channel 4 being occupied by the neutral solution.

To determine the concentration profile obtained at the upper side 61 of the base 6, on which living cells that are to be stimulated are likely to be arranged, the microfluidic device 1 was then observed with an optical means 18 belonging to the microfluidic system according to the invention.

The concentration profile obtained on the upper side 61 of the base 6 has the form of a representative curve of a function of the "erf" type. This form is obtained by the diffusion of the neutral and fluorescent solutions through the microporous membrane 5, and then through the chamber 8.

With the fluid supplying means 50 of the "co-flow" type, it is therefore possible to obtain a quite particular concentration profile at the base of the chamber 8, and therefore on the living cells that are to be stimulated.

Figure 7A:
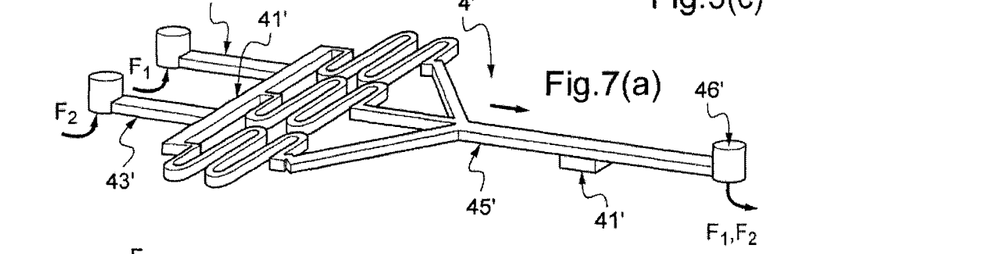
FIG. 7(a) shows another microfluidic channel of the microfluidic device according to the invention.
Figure 7B:
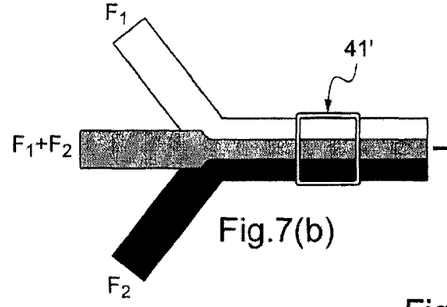
FIG. 7(b) shows fluids flowing in this first channel and FIG. 7(c) shows a concentration profile obtained in a chamber of the device according to the invention.
Figure 7C:
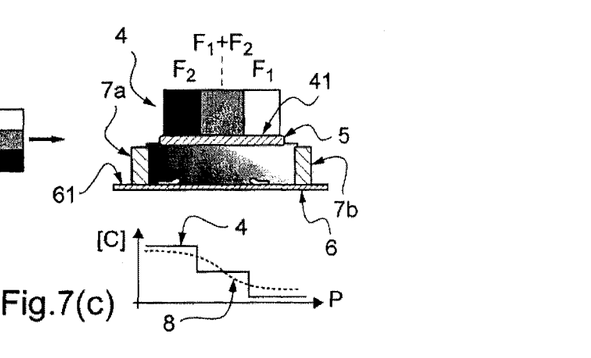

Another form of microfluidic channel 4' is shown in FIGS. 7(*a*) to 7(*c*).

The fluids $F_1$, $F_2$ are conveyed in two branches 42', 43' which both lead into one and the same channel 44' having three outlets leading to three tubing coils (not referenced). The first fluid $F_1$ goes via a first outlet and is directed to a first tubing coil, the second fluid $F_2$ goes via a second outlet and is directed to a second tubing coil, a mixture of the two fluids $F_1$ and $F_2$ finally going via a central outlet of channel 44' and being directed to a central stubing coil. At the outlet of the serpentine tubes, the fluids are combined in a common branch 45' having an interface 41' with the microporous membrane 5 of the microfluidic device 1 according to the invention.

The end 46' of the common branch 45' has an outlet for the fluids $F_1$, $F_2$.

FIG. 7(b) is a schematic representation of the flow of the fluids $F_1$, $F_2$ in the different branches of the microfluidic channel 4'. The different fluids flow in the microfluidic channel 4 in a laminar regime.

We then speak of fluid supplying means of the "tri-flow" type.

FIG. 7(c) shows, in a sectional view, the behavior of the fluids at the interface 41'. The experimental device used for this purpose is similar to that presented above for the microfluidic channel 4 of the "co-flow" type.

FIG. 7(c) notably shows that the concentration profile in the microfluidic channel 4' has a staircase shape. It also shows that the concentration profile obtained on the upper side 61 of the base 6 (optically transparent) has a linear central zone, which can be used for stimulating certain target cells.

Thus, with this microfluidic channel 4' of the "tri-flow" type, it is possible to apply a linear concentration profile at the center of the cover on the living cells that are to be stimulated.

The microfluidic system according to the invention is not limited to the use of first microfluidic channels 4, 4' designed just according to the "co-flow" or "tri-flow" types described above. Thus, other types of first microfluidic channels can be envisaged depending on the concentration profile that we wish to apply on the living cells.

The microfluidic system according to the invention thus permits a much easier control of a concentration profile of molecules likely to stimulate a target, such as living cells.

Thus, a variation in flow rate of either of the fluids $F_1$, $F_2$ does not cause a substantial change of the concentration profile of molecules applied to the living cells.

One reason is connected with the fact that the living cells are not located on the microporous membrane 5, but on the base 6 of the chamber 8. Indeed, as the living cells are arranged opposite the membrane 5, the time for diffusion through the chamber 8 attenuates the possible perturbations of the flow of the fluids in the microfluidic channel 4.

FIGS. 5(c) and 7(c) show, as examples, different concentration profiles likely to be applied to the living cells.

The design of the microfluidic system according to the invention also displays a dynamic behavior, allowing numerous tests to be performed quickly.

This is demonstrated by the tests described below, carried out in a dynamic regime.

For these tests, the microporous membrane 5 is a membrane of the Whatman Cyclopore type with 400 nm pores. The culture chamber has a height h'=200 µm and a width of 1 mm.

A first fluid $F_1$ (neutral solution) was circulated in the microfluidic channel 4, then a second fluid $F_2$ was circulated in this same channel 4, the fluid $F_2$ in this case being formed by a fluorescent solution comprising molecules having a diffusion coefficient comparable to the molecules usually used to stimulate living cells.

Figure 8:
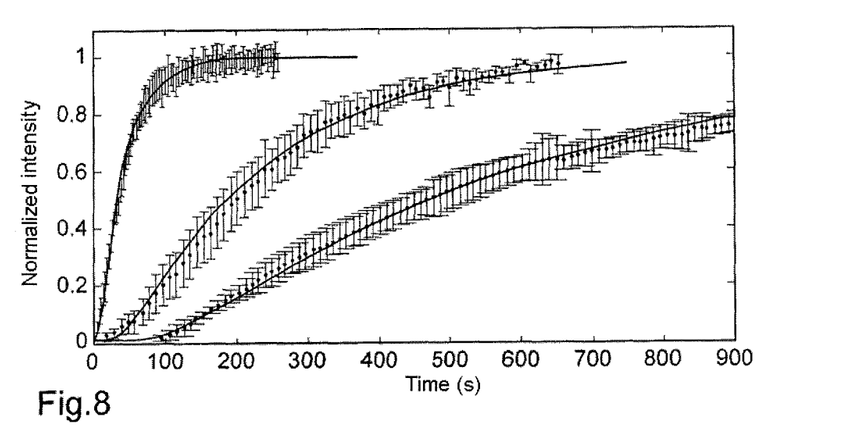
FIG. 8 shows the variation over time for establishing, by diffusion, a permanent regime of molecules intended to stimulate living cells, for different solutions.

The results obtained for three fluorescent solutions (fluorescein, GFP and Dextran70MW) are shown in FIG. 8.

FIG. 8 shows the variation of the normalized intensity of the fluorescent solution measured with an optical means such as a confocal microscope positioned behind the base 6, as a function of time. Measurement with the microscope is performed at the base 6, which is in this case a glass slide.

The origin of each of the three curves (t=0s) shown in FIG. 8 corresponds to the beginning of the circulation of the second fluid $F_2$.

It can be seen that the time for establishment of the concentration profile at this glass slide is between a few tens of seconds and a few minutes, depending on the nature of the fluorescent solution. Logically, the larger the molecules contained in this solution, the longer the time for establishment.

In general, it is seen that the times for establishment are relatively short, comparable to those for a diffusion over a distance of the order of the height h' of the chamber 8 (culture chamber) and allow to carry out an experiment rapidly, with a stable concentration profile.

Since the microfluidic system allows to carry out the culture of the living cells independently, the tests can be carried out quickly, in a time typically between 1 h and 2 h. Then, it is possible to move on to another test, with another culture.

This is not conceivable with the microfluidic system shown in FIG. 1. Indeed, in this case, the culture is carried out within the microfluidic system, so that times of several days are required for carrying out a test.

Generally, the microfluidic system will comprise an optical device for visualizing the culture chamber 8 through the base 6. When such an optical device is provided, the base is advantageously made of an optically transparent material. It is thus easier to follow the response of living cells arranged on this base 6 to a stimulation by certain molecules.

Figure 9:
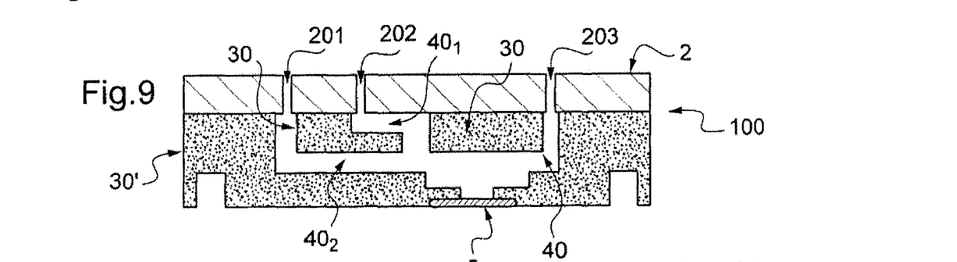
FIG. 9 is a diagram, in a sectional view, of an embodiment of the microfluidic device according to the invention, enabling concentration profiles to be generated that are more complex than with the microfluidic device shown schematically in FIG. 2.

FIG. 9 shows an embodiment of the microfluidic device according to the invention, in a partial sectional view. Indeed, FIG. 9 only shows the upper part of the microfluidic device, an assembly comprising a base (likely for example to receive a culture of living cells) and side walls likely to form a chamber under the microporous membrane 5 being necessary so that the microfluidic device 100 can be used.

The microfluidic device 100 has characteristics similar to the microfluidic device 1 described with reference to FIG. 2 and can, in this case, be used with a microfluidic channel 40 of the "co-flow" or "tri-flow" type.

The microfluidic channel 40 can be supplied by a fluids supplying means such as the one described above.

However, the structure of the microfluidic channel is modified. Indeed, in this embodiment, the microfluidic channel 40 is organized on several levels, in this case two levels $40_1$, $40_2$ in the example shown in this FIG. 9. Each level comprises a fluid inlet corresponding to an orifice 201, 202 formed in the cover 20, with a common fluid outlet 203.

An advantage in using a microfluidic device comprising a microfluidic channel on several levels is that it allows the application of more complex concentration profiles of molecules likely to stimulate living cells. For example, we can envisage using concave, convex or periodic concentration profiles in the chamber 8, while still keeping a limited number of inlets and outlets for the fluids.

Figure 10:
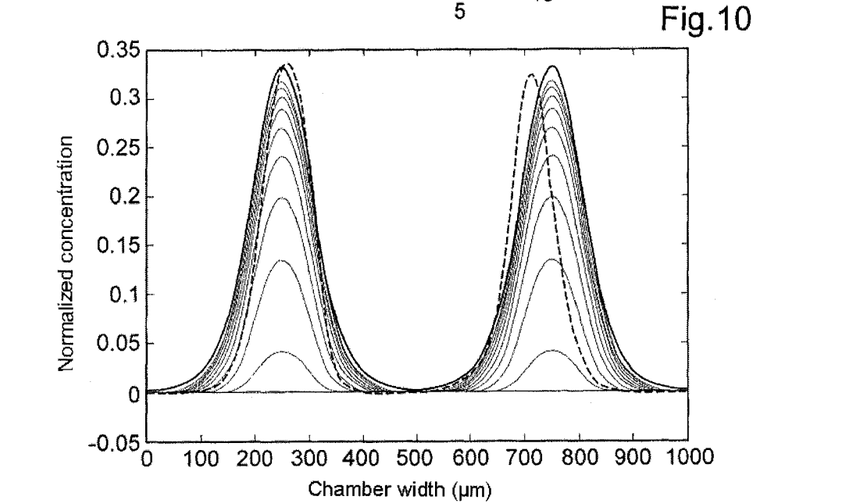
FIG. 10 shows a spatially periodical concentration profile, likely top be obtained in the chamber of the microfluidic device according to FIG. 9.

Furthermore, FIG. 10 shows the result of a simulation obtained with a microfluidic device comprising a channel 4 on two levels, allowing to obtain a spatially periodic concentration profile. The width of the chamber 8 is shown on the abscissa, and the normalized concentration of stimulation molecules is shown on the ordinate. The different solid curves show the variation over time of the simulated concentration profile up to stabilization. The dotted curve corresponds to the experimental data obtained with a flow of fluorescein.

In particular, to achieve a given concentration profile applied periodically, it is conceivable to introduce fluids $F_1$, $F_2$ with a supplying means of the "co-flow" type in the first level $40_1$ (via the orifice 202) of the microfluidic channel, then introduce at regular intervals, for example with another supplying means of the "co-flow" type, other fluids $F'_1$, $F'_2$ in the second level $40_2$, via the orifice 201.

This is notably possible because of the process of manufacture used, which allows to structure microfluidic channels of any shape above the microporous membrane 5.

It is understood that the first channel 40 could have more than two levels, depending on the complexity of the concentration profile that we wish to apply.

The manufacture of the structure shown in FIG. 8 is based on an adaptation of the process described above.

Figure 11A:
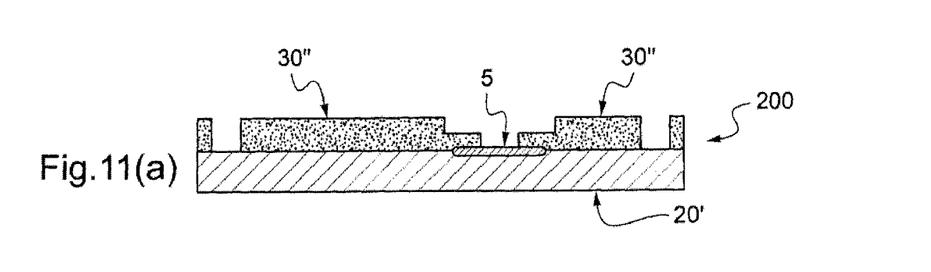
FIGS. 11(a) to 11(c) show several intermediate structures obtained in a process of manufacture of the microfluidic device shown in FIG. 9.

Steps (a) and (b) are thus carried out for producing the structure 200 shown in FIG. 11(a). The substrate used in these steps is referenced 20' and a side wall 30" closed at its base by the microporous membrane 5.

Figure 11B:
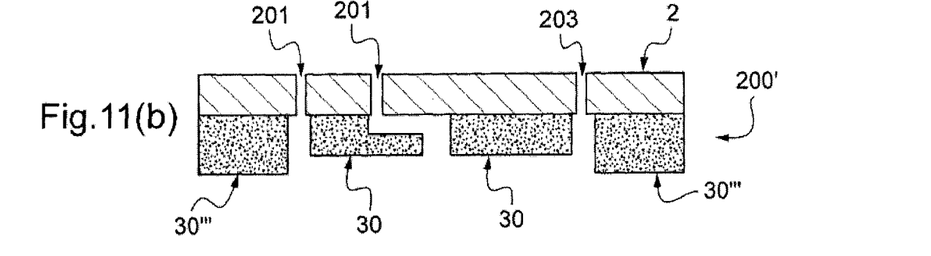

The structure 200' shown in FIG. 11(b) is then produced using steps similar to steps (a) to (c) given above. The structure 200' comprises four first side walls 30, 30''' fixed on a cover 2 provided with three orifices 201, 202 (for the fluid inlet) and 202 (or the common outlet of the fluids). In this case, no microporous membrane is provided at the base of the side wall 30, since the level $40_1$ of the microfluidic channel 40 must be in fluid communication with the second level $40_2$ of this same microfluidic channel 40.

Figure 11C:
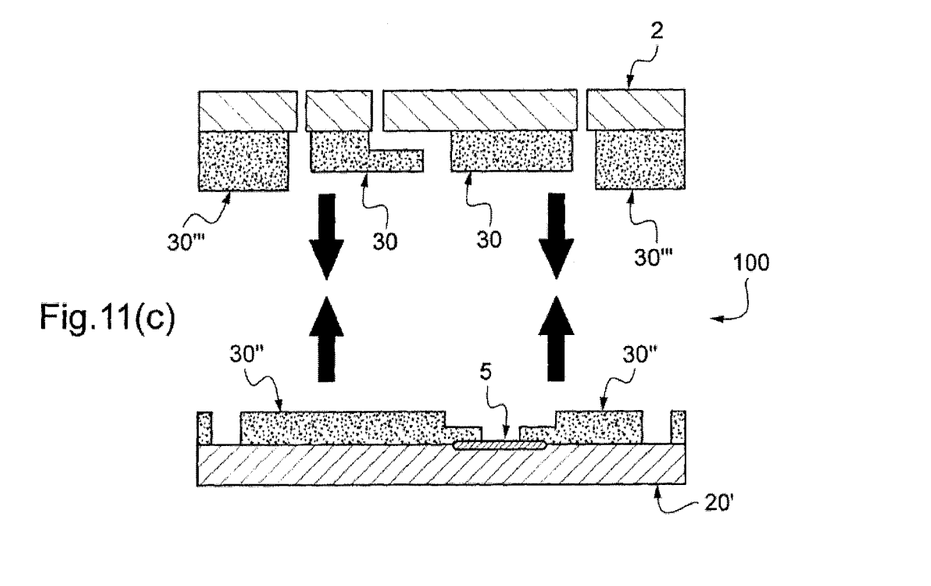

The structures 200 and 200' are then fixed one to the other, as is shown in FIG. 11(c). This fixation can be carried out by photo-irradiation or heating, so that the side walls 30" and 30' are fixed together to form the side wall 30'. This step thus allows to form the second level $40_2$ of the microfluidic channel 40.

Finally a step similar to step (d) is carried out for an assembly comprising two second side walls of a photo-cured and/or thermally cured resin in order to form the chamber under the microporous membrane. A process repeating steps ($e_1$) to ($e_3$) described above with reference to FIGS. 4(a) to 4(c) is carried out for this purpose.

It should be noted that the devices 1, 100 described previously comprise a chamber 8 (naturally closed when stuck to the microfluidic channel 4, 40), in which the living cells are located. This chamber 8 could comprise a culture gel, although advantageously this will not be the case. Moreover, this chamber can be replaced by a microfluidic channel, therefore comprising openings advantageously arranged laterally. In this latter case, the microfluidic device will then comprise the microfluidic channel 4, 40 in which the fluid circulates and another microfluidic channel in which the living cells are located.

There are therefore multiple possibilities offered by the microfluidic system according to the invention.

In particular, it is possible to apply a concentration gradient of molecules intended to stimulate living cells, having the desired shape (the examples given above show a gradient in the form of an "erf" function, or a gradient of linear shape in the central part of the chamber 8 of the device 1, 100) at these living cells. The concentration profile becomes established in the chamber 8, the living cells being arranged on a base of the device located away from the microporous membrane 5, and more precisely, opposite this membrane 5 within the chamber 8 (it being possible to replace this chamber with a microfluidic channel).

Thus, the application of this profile is not carried out at a fluid supplying means. The fluid supplying means is then simple and only supplies fluids whose flow rate can vary slightly without any appreciable variation of the concentration profile applied at the living cells. The control of the concentration profile at the living cells is therefore easier, and less sensitive to the possible perturbations external to the microfluidic system.

It is thus possible to obtain a stable concentration profile in the chamber 8, in particular at the base 61 of this chamber, after a time for stabilization that depends mainly on the height of the chamber and the diffusion coefficient of the stimulation molecules.

The process of manufacture of the microfluidic device according to the invention also allows to use a base made of an optically transparent material, for example a glass slide on which a cell culture can be carried out according to a standard procedure. The observation of the behavior of the living cells (growth, etc.) can thus be performed easily with a optical visualization means positioned behind the glass slide.

The optical observation can be performed at high spatial resolution since the base made of an optically transparent material can be very thin. For example, high resolution, or even super-resolution fluorescence microscopy, obtained with techniques such as photoactivated localization microscopy (PALM) or stimulated emission depletion microscopy (STED), using a base formed from a glass slide with a thickness of 150 μm, can be carried out.

At the same time, this visualizing means allows to know the concentration profile of the stimulation molecules applied to the living cells. It is therefore much easier for correlations between the observed behavior of the living cells and the concentration profile applied to them to be carried out experimentally.

Finally, numerous tests can be carried out rapidly.

The invention may be used in particular in the field of biology, for the culture, the observation and the study of living cells. In particular, the chemotactic response of nerve cells to certain molecules can be determined, for example in order to create neural networks. In particular, it is also possible to measure the response of cancer cells to molecules used for chemotherapy. The microfluidic system can also be used to make biochips.

The advantages associated with the invention may be interesting for other fields of application, for example for determining the toxicity thresholds of certain molecules in cosmetology.

The invention claimed is:

1. A microfluidic system comprising:
a microfluidic device comprising at least one microfluidic channel having at least:
a first branch provided with an inlet orifice for a first fluid,
a second branch provided with an inlet orifice for a second fluid comprising molecules likely to stimulate a target;
a common branch for said fluids, provided with an outlet orifice for said fluids, the first and second branches combining in the common branch;
at least one fluid source connected to the inlet orifices of the at least one microfluidic channel for supplying the channel with said fluids;
at least one chamber or another microfluidic channel having a base configured to receive the target, wherein the target is formed by a set of living cells; and
at least one microporous membrane arranged at an interface of the common branch upstream from the outlet orifice, said microporous membrane being positioned to separate the at least one chamber or the other micro fluidic channel from the common branch at least one microfluidic channel,
said microporous membrane being impervious to said fluids and configured to prevent said fluids from going through to the other side of the membrane and to allow said molecules to diffuse therethrough;
said microporous membrane not directly contacting the base so that when the at least one fluid source supplies the at least one microfluidic channel with said fluids, the diffusion of molecules likely to stimulate the target occurs, after going through the microporous membrane, then through the at least one chamber or said other microfluidic channel, and wherein after the diffusion of the molecules likely to stimulate a reaction with the target in the chamber or the other micro fluidic channel, a concentration profile in the at least one chamber or the other microfluidic channel is generated.

2. The microfluidic system according to claim 1, wherein the microfluidic channel comprises a cover made of a material selected from the group consisting of: glass or silicon, a non-elastomeric photocrosslinked polymer, a metal, an alloy that is an electrical conductor or semiconductor, a ceramic, quartz, sapphire, and an elastomer.

3. The system according to claim 1, wherein said at least one inlet orifice and said at least one outlet orifice for the fluids are formed in the cover.

4. The microfluidic system according to claim 1, wherein the microfluidic channel comprises at least one wall made of a photo-cured and/or thermally cured resin.

5. The microfluidic system according to claim 1, wherein the microporous membrane extends transversely on the side wall of the microfluidic channel to close the bottom of said channel.

6. The microfluidic system according to claim 1, wherein the microfluidic channel is organized on several levels, each level having at least one inlet orifice for at least one fluid.

7. The microfluidic system according to claim 1, wherein the base of the chamber or of said other microfluidic channel is made of an optically transparent material.

8. The microfluidic system according to claim 1, wherein the chamber or said other microfluidic channel comprises side walls made of a photo-cured and/or thermally cured resin.

9. The microfluidic system according to claim 8, wherein the microporous membrane extends transversely between the side walls (7a, 7b) of the at least one chamber or of said other microfluidic channel, to close a top of said at least one chamber or of said other microfluidic channel.

10. The microfluidic system according to claim 1, wherein the microporous membrane is made of a material selected from a group consisting of: glass, polycarbonate, polyester, polyethylene terephthalate, quartz, silicon, silica and silicon carbide.

11. The microfluidic system according to claim 1, wherein the microporous membrane comprises pores at a density between $10^3$ and $10^{10}$ pores/cm$^2$.

12. The microfluidic system according to claim 1, wherein the pores have a hydraulic diameter between 0.05 μm and 12 μm.

13. The microfluidic system according to claim 1, wherein an optical visualization means is provided.

14. The microfluidic system according to claim 13, wherein the optical visualizing means uses a technique selected from the group consisting of photoactivated localization microscopy and stimulated emission depletion microscopy.

15. The microfluidic system according to claim 1, wherein the first and second fluids only differ by the concentration of stimulation molecules.

16. The microfluidic system according to claim 15, wherein the first and second fluids only differ by the presence of stimulation molecules.

17. The microfluidic system according to claim 1, wherein the first and second fluids flow in the common branch in a laminar regime.

18. The microfluidic system according to claim 1, comprising a third branch provided with an inlet orifice for a third fluid comprising stimulation molecules, wherein the first, second and third branches combine in the common branch, wherein the third fluid flows in the common branch between the first and second fluids, and wherein the concentration of stimulation molecules in the third fluid is comprised between the concentration of stimulation molecules in the first fluid and the concentration of stimulation molecules in the second fluid.

19. The microfluidic system according to claim 18, wherein the third fluid is a mixture of the first and second fluids.

20. A method for controlling a concentration profile of molecules likely to stimulate a target comprising:
   providing a microfluidic system according claim 1;
   placing the target on the base, wherein the target is formed by a set of living cells;
   supplying the first branch with a first fluid;
   supplying the second branch with a second fluid comprising molecules, the first and second branches combining in the common branch;
   wherein, when the fluids are supplied, the diffusion of molecules likely to stimulate the target occurs, after going through the microporous membrane, through the at least one chamber or said other microfluidic channel, and wherein, after the diffusion of the molecules likely to stimulate a reaction with the target, a concentration profile in the at least one chamber or the other microfluidic channel is generated.

* * * * *